United States Patent [19]
Ahlers

[11] Patent Number: 5,178,201
[45] Date of Patent: Jan. 12, 1993

[54] METHOD FOR PRODUCING AN IMPLANT WITH AN OPEN-CELLED METAL STRUCTURE

[75] Inventor: Olaf Ahlers, Hamburg, Fed. Rep. of Germany

[73] Assignee: Eska Medical GmbH & Co., Luebeck, Fed. Rep. of Germany

[21] Appl. No.: 845,303

[22] Filed: Mar. 3, 1992

[30] Foreign Application Priority Data

Mar. 5, 1991 [DE] Fed. Rep. of Germany ....... 4106971

[51] Int. Cl.$^5$ .............................................. B22D 7/02
[52] U.S. Cl. ........................................ 164/34; 164/35; 164/45
[58] Field of Search ................ 164/34, 35, 36, 45, 164/246; 249/61, 62

[56] References Cited

U.S. PATENT DOCUMENTS 4,600,546  7/1986  Grundei ................................ 164/35
5,016,702  5/1991  Ahlers ................................... 164/34
5,042,560  8/1991  Ahlers ................................... 164/34

FOREIGN PATENT DOCUMENTS 0290664  11/1990  Japan ................................... 164/34

Primary Examiner—Richard K. Seidel
Assistant Examiner—Erik R. Puknys
Attorney, Agent, or Firm—Panitch Schwarze Jacobs & Nadel

[57] ABSTRACT

An implant is produced with an open-celled structure at least partly covering its surface. The method uses a positive pattern having a basic pattern with particles bonded to it, the particles covering the areas of the pattern which correspond to the structured surface areas of the implant. The method uses the usual steps of conventional lost positive casting techniques. Importantly, the particles have a base with four to eight pins extending radially from its surface with at least three being connected to the basic pattern (e.g., by adhesive).

9 Claims, 1 Drawing Sheet

METHOD FOR PRODUCING AN IMPLANT WITH AN OPEN-CELLED METAL STRUCTURE

FIELD OF THE INVENTION

The invention relates to a method for producing implants with an open-celled metal structure at least partly covering its surface.

BACKGROUND OF THE INVENTION

Implants of this type allow bone material to grow into the open-celled surface structure, thereby assuring permanent fixation in the bone. A similar method is disclosed in DE-OS 27 30 004. It is particularly suggested therein that, for the creation of an uneven surface next to the positive pattern and ultimately next to the implant produced by the method as a metallic image of the pattern, particles in the form of small balls be adhered to the basic pattern. The implant has on the areas with uneven surfaces raised spherical segment-shaped elevations with back cuts. After implantation, bone material can grow in these surfaces and serve for permanent fixation of the implant into the bone.

Even if this may be successful in practice, the implants manufactured according to the stated procedure have the following disadvantages:

The growing of bone material is indeed possible, but medical research has shown boundary layer problems which cause malnourishment to the bone because of a missing substrate flow, so that lasting bony fixation of the implant becomes questionable. Also, the surface of the implant is still relatively smooth, whereby the primary stability of the implant right after the implantation is very low.

Behind the stated procedure lies the medical philosophy that it should be possible for an implant to be removed during corrective surgery which may become necessary, perhaps due to an infection, without destroying the bone that surrounds the implant. In the past years a new operation technique has been developed, which allows corrective surgery for the removal of the implant which is grown through with bone material (DE 32 24 265 A1), in which the bone is split, the implant removed, a new implant inserted, and the bone halves are rejoined and ultimately grow together again.

According to the above-cited reference it is suggested to make an implant according to the conventional lost positive technique, whereby an open-celled plastic molded body, e.g., a sponge, is used as a positive pattern. It is to be be observed in such foams that the strength of the webs enclosing the cells is a function of the cell width. This is a necessary consequence of the production of such foams and cannot be controlled. It has been found that the webs formed from use of such fine pieces are too thin, on account of which the above reference suggests strenthening of these webs by means of flowing wax or by means of a wax-water emulsion.

This layering procedure is relatively difficult to control. Additionally, despite a globally relatively constant form, the sponge also exhibits local peculiarities, such as smaller cells. This circumstance manifests itself in a negative manner during the casting process after the hardening of the poured metal into the negative cavity and upon removal of the ceramic mass. When one considers that the finished implants must have the highest purity in order to be implanted, it is extremely difficult to remove the last traces of the embedding mass of the cast, especially if by chance there are smaller cells in the spatial depths.

DE 90 11 363.2 U1 discloses another prosthetic part made according to the lost postive casting technique. As a positive pattern, a base with an adhered lattice element, preferably made of wax, is used. The lattice element is made by an injection molding process and is wrapped like a mat around the base. For this the lattice element must be elastic enough, or it will break. Due to this the webs of the lattice element have a preferred thickness of 0.05 cm. The webs of the lattice-shaped surface of the implant will then of course have a comparable order of magnitude after completion of the molding. If the webs must have a greater thickness, then a layering procedure of the type described above must again be considered.

Additional procedures are described in DE 39 17 033 C1 and DE 39 28 394 C2 (U.S. Pat. Nos. 5,042,560 and 5,016,702, respectively) of the present inventor. Therein it is suggested that the webs of an open-celled plastic substrate (sponge), which is formed on a wax base and creates together therewith the positive pattern of the molded piece (implant) to be produced, are to be strengthened by a layer of a two-component silicone (U.S. Pat. No. 5,042,560) or a poly(methyl methacrylate) or polyester resin (U.S. Pat. No. 5,106,702).

An object of the present invention is to develop a process which improves the above-cited art so that the surface structures of the implant created by the process are discrete and so stable, that an additional treatment of the positive pattern is not necessary, and that difficulties do not appear upon removal of the ceramic embedding mass after the molding process because of local deviations of the structures.

SUMMARY OF THE INVENTION

These objects are achieved by the present invention which is characterized by the shape of the particles to be attached to the basic pattern. These particles have a ball-shaped, double cone, double pyramid or similar basic shape with from four to eight, preferably six, pins extending radially therefrom, of which at least three of the pins are bonded to the basic pattern. The interstice between the at least three pins bonded to the basic shape form, after completion of the process, an open cell in the surface structure of the implant, in which bone material is maintained by the life-sustaining substrate flow.

All the particles of a positive pattern have the same shape, which can be made, for example, by injection molding. This globally constant form brings about a considerable simplification during removal of the ceramic embedding mass after the casting.

After the completion of the procedure each particle forms an individual part of the implant, whereby as an additional important advantage the high dimensional accuracy of the implant is to be mentioned. Additional measures for increasing the stability of the pins are not necessary, since the thickness of the pins of the particles can be controlled from the beginning during the manufacturing process. Preferred are pins with a thickness in the range of 0.6 to 1.6 mm.

Particularly advantageous is the use of particles having a symmetrical shape and having six pins equidistantly spaced and extending like rays from the surface of the ball-shaped, double pin or double pyramide-shaped basic body. One can picture this particle as a crystal point in a crystal matrix, in which the basic body takes the place of an atom and the pins are the connections to a neighboring atom.

In the above-described case, the ends of three pins are bonded to the basic pattern, the other three point away from the basic pattern and insure an extreme surface aggressiveness in the finished implant, in the sense that an excellent primary stability and an extreme stimulus of the surrounding bone are provided. The latter stimulate the bone for quick growing into the surface structure.

The final thickness of the implant to be made can be varied by using a standard basic pattern, in which several layers of particles are attached to the positive pattern. In this case the particle structure is visually similar to the structure of a crystal lattice. All of the above-mentioned advantages are retained by carrying out the described process.

So that the particles can be completely removed during the heating of the pattern, they comprise one of the following materials: wax, polypropylene, polyethylene, poly(methyl metacrylate) or any other suitable material.

BRIEF DESCRIPTION OF THE DRAWINGS

The foregoing summary of the invention, as well as the following detailed description of the preferred embodiment, will be better understood when read in conjunction with the appended drawings. For the purpose of illustrating the invention, there is shown in the drawings an embodiment which is presently preferred, it being understood, however, that the invention is not limited to the specific arrangement and instrumentalities disclosed.

DETAILED DESCRIPTION OF PREFERRED EMBODIMENT

Figure 1:
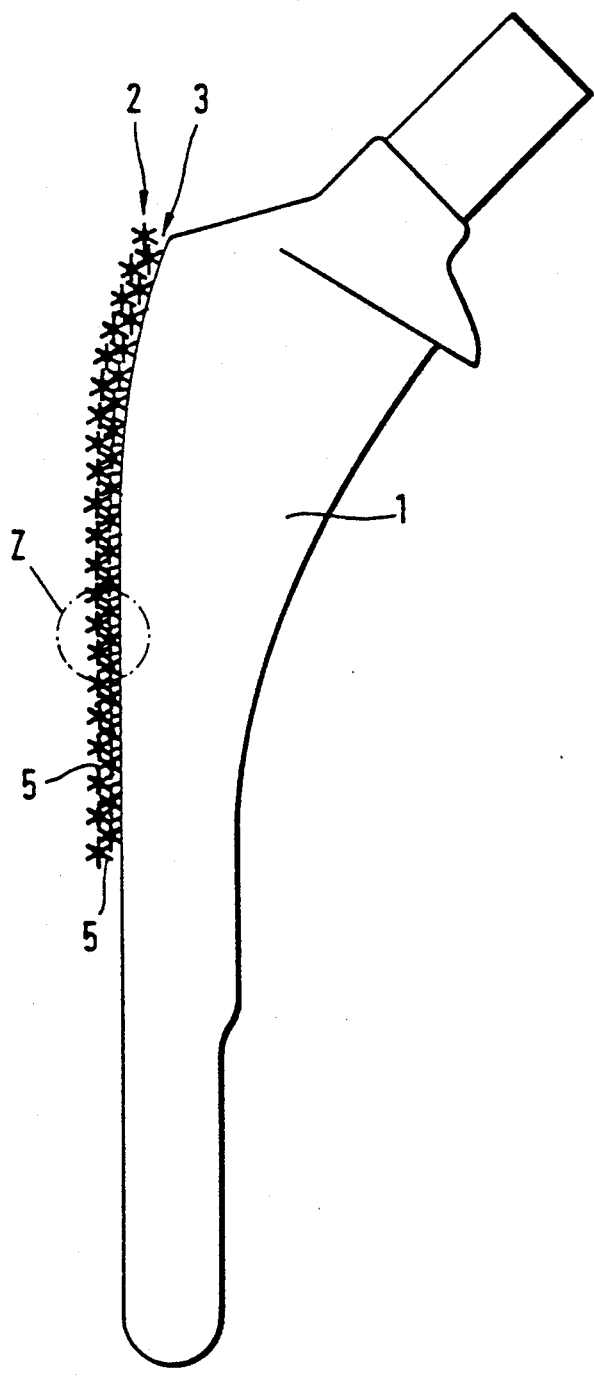
FIG. 1 is a view of a positive pattern for a hip joint shaft having on one surface particles according to the invention.

FIG. 1 shows a view of a positive pattern of a hip joint shaft using the process of the invention. The positive pattern consists of a basic pattern 1, as well as particles 5 attached thereto. In the embodiment shown two layers 2 and 3 of particles 5 are displayed. The area of the basic pattern 1, provided with the particles 5, is only shown as exemplary.

Figure 2:
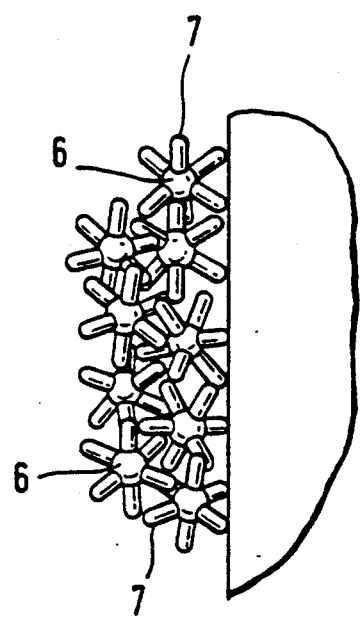
FIG. 2 is an enlarged view of detail Z in FIG. 1.

Details of the particle arrangement on the basic pattern 1 are shown in FIG. 2, which displays the enlargement of detail Z in FIG. 1. Clearly recognizable here is the form of the particles used. These exhibit a ball-shaped basic body 6, from which six evenly distributed pins 7 extend radially away from the surface. Displayed are two layers of particles, which lie on top of each other. The outer layer is keyed into the lowest layer which is attached to the basic pattern 1.

It will be understood by those skilled in the art that the positive pattern with attached particles according to the present invention may be used in conventional lost positive casting methods, such as those described above. Such methods typically include the steps of forming a basic pattern from an incinerable or meltable material with incinerable or meltable particles bonded to the pattern in the areas which correspond to the structured surface areas (i.e., open-celled structure) of the resulting implant to be produced, embedding the positive pattern as a whole in a ceramic embedding mass, heating the pattern to incinerate or melt the basic pattern as well as the particles attached thereto, while at the same time firing or baking the ceramic embedding mass, pouring molten material (usually metal) into the remaining cavitity formed in the ceramic mass by incinerating or melting the basic pattern and particles, and after hardening the molten material, removing the ceramic embedding mass to leave the implant with its open-celled surface structure.

After the casting a metal image corresponding to the positive pattern is obtained. By construction of the positive pattern according to the Figures an implant is obtained with an open-celled network structure in the areas of its surface. Because of the uniformity of the open cells, removal of the ceramic embedding mass is possible without problems.

While a number of variations of the embodiment shown in the drawings will be apparent to those skilled in the art, it is preferred that the particles be symmetrically shaped, that the basic body have a diameter of 1.5 to 3 mm, and that the length of the radially extending pins be about 0.8 to 1.6 mm. Moreover, while only two layers 2, 3 of particles 5 are shown in the drawings, up to four layers or more may be bonded on top of each other. The particles may be bonded to the basic pattern and the layers to each other by any suitable means, such as adhesive.

The present invention may be embodied in other specific forms without departing from the spirit or essential attributes thereof and, accordingly, reference should be made to the appended claims, rather than to the foregoing specification as indicating the scope of the invention.

I claim:

1. In a method for producing an implant with an open-celled structure at least partially covering its surface by usage of a positive pattern, comprising the steps of forming an incinerable or meltable basic pattern with incinerable or meltable particles bonded to said pattern in the areas which correspond to structured surface areas of the resulting implant, embedding the positive pattern as a whole in a ceramic embedding mass, heating the pattern, whereby the basic pattern is incinerated or melted, the particles are incinerated or melted, and the ceramic embedding mass is baked, molten material is poured into the remaining cavity, and after hardening of the molten material the ceramic embedding mass is removed, the improvement comprising that the particles (5) have a basic body (6) from which four to eight pins (7) extend radially, of which at least three pins are adhered to the basic pattern.

2. A method according to claim 1 wherein the particles (5) are symmetrically shaped and have six equidistantly spaced pins (7) radially extending from the basic pattern (6).

3. A method according to claim 1 wherein the basic body (6) of particles (5) has a diameter of 1.5 to 3 mm and the length of the radially extending pins (7) is 0.8 to 1.6 mm.

4. A method according to claim 1 wherein several layers (2,3) of particles (5) are bonded to the basic pattern.

5. A method according to claim 4 wherein up to four layers of particles are bonded on top of each other.

6. A method aocording to claim 1 wherein the particles (5) comprise wax.

7. A method according to claim 1 wherein the particles (5) comprise polypropylene.

8. A method according to claim 1 wherein the particles (5) comprise polyethylene.

9. A method according to claim 1 wherein the particles (5) comprise poly (methyl methacrylate).

* * * * *